(12) United States Patent
Yoshida et al.

(10) Patent No.: US 9,757,322 B2
(45) Date of Patent: Sep. 12, 2017

(54) LIQUID COSMETIC

(71) Applicant: SHISEIDO COMPANY, LTD., Tokyo (JP)

(72) Inventors: Kyoko Yoshida, Yokohama (JP); Kazunobu Suzuki, Yokohama (JP); Akinori Ono, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/372,532

(22) PCT Filed: Dec. 10, 2012

(86) PCT No.: PCT/JP2012/081889
§ 371 (c)(1),
(2) Date: Jul. 16, 2014

(87) PCT Pub. No.: WO2013/108513
PCT Pub. Date: Jul. 25, 2013

(65) Prior Publication Data
US 2014/0356401 A1 Dec. 4, 2014

(30) Foreign Application Priority Data
Jan. 17, 2012 (JP) .................................. 2012-006911

(51) Int. Cl.
| | | |
|---|---|---|
| *A61K 8/06* | (2006.01) | |
| *A61Q 19/00* | (2006.01) | |
| *A61K 8/81* | (2006.01) | |
| *A61K 8/86* | (2006.01) | |
| *A61K 8/34* | (2006.01) | |
| *A61K 8/84* | (2006.01) | |
| *A61K 8/37* | (2006.01) | |
| *A61K 8/39* | (2006.01) | |
| *A61K 8/92* | (2006.01) | |
| *A61Q 19/02* | (2006.01) | |

(52) U.S. Cl.
CPC ............ *A61K 8/8147* (2013.01); *A61K 8/062* (2013.01); *A61K 8/068* (2013.01); *A61K 8/345* (2013.01); *A61K 8/375* (2013.01); *A61K 8/39* (2013.01); *A61K 8/84* (2013.01); *A61K 8/86* (2013.01); *A61K 8/922* (2013.01); *A61Q 19/00* (2013.01); *A61Q 19/007* (2013.01); *A61K 2800/21* (2013.01); *A61Q 19/02* (2013.01); *Y10S 977/773* (2013.01)

(58) Field of Classification Search
CPC ........... A61K 8/06; A61K 8/062; A61K 8/068
See application file for complete search history.

(56) References Cited

U.S. PATENT DOCUMENTS

| | | | |
|---|---|---|---|
| 2004/0071651 A1 | 4/2004 | Deckner et al. | |
| 2006/0233721 A1* | 10/2006 | Tamarkin ............... | A61K 8/046 424/47 |
| 2009/0081142 A1* | 3/2009 | Omura ................... | A61K 8/06 424/60 |
| 2011/0250246 A1* | 10/2011 | Suzuki et al. ............... | 424/401 |
| 2012/0022160 A1* | 1/2012 | Suzuki et al. ............... | 514/561 |

FOREIGN PATENT DOCUMENTS

| | | | |
|---|---|---|---|
| DE | 10 2007 045 165 | 4/2009 | |
| DE | 102007045165 A1 * | 4/2009 | ............... A61K 8/06 |
| EP | 2 177 201 | 4/2010 | |
| JP | 09-157129 | 6/1997 | |
| JP | 11-049684 | 2/1999 | |
| JP | 2009-234960 | 10/2009 | |
| JP | 2009242326 | 10/2009 | |
| JP | 2009-286757 | 12/2009 | |
| JP | EP 2177201 A1 * | 4/2010 | ........... A61K 8/0295 |
| JP | 2011032193 | 2/2011 | |
| WO | WO 2009/016989 | 2/2009 | |
| WO | WO 2010/044261 | 4/2010 | |
| WO | WO 2010044261 A1 * | 4/2010 | |

OTHER PUBLICATIONS

TF Tadros. "Applied Surfactants: Principles and Applications." ISBN: 3-527-30629-3, copyright 2005, pp. 1-17 included.*
ICI Americas Inc. "The HLB System a time-saving guide to emulsifier selection." ICI Americas Inc., Wilmington, DE, Mar. 1980, pp. 1-22.*
A Heptner, R Kropke, K Luttig, J Nielsen, J Dr. Schulz. English Translation of Patent DE102007045165 A1. Google Patents. http://google.com/patents/DE102007045165A1?cl=en, accessed Jan. 11, 2016, 10 printed pages.*
RN Gursoy, S Benita. "Self-emulsifying drug delivery systems (SEDDS) for improved oral delivery of lipophilic drugs." Biomedicine & Pharmacotherapy, vol. 58, 2004, pp. 173-182.*
ICI Americas Inc. "The HLB System" A Time-Saving Guide to Emulsifier Selection. ICI Americas Inc., Wilmington DE, Revised Mar. 1980, pp. 1-22.*
PCT/JP2012/006911 International Search Report, dated Mar. 2, 2013, 2 pages—English; 2 pages—Japanese.
Shigeru Sekine (representative), Hiroaki Tamura (editor) et al., Shin Keshohin Handbook, Nikko Chemcials Co., Ltd., Oct. 30, 2006 (30.10.1006), pp. 507 to 511.

(Continued)

*Primary Examiner* — Isaac Shomer
(74) *Attorney, Agent, or Firm* — Andrew F. Young, Esq.; Lackenbach Siegel, LLP

(57) ABSTRACT

A liquid cosmetic which minimizes stickiness or stiffness caused by the incorporation of a large amount of a moisturizing agent is provided. This liquid cosmetic contains 10 to 40% by mass of a moisturizing agent (a), 0.01 to 3% by mass of an oil (b), 0.01 to 5% by mass of a hydrophilic surfactant (c), and 0.001 to 0.3% by mass polyacrylic acid or a metal salt thereof (d), and wherein an average emulsified particle size is 500 nm or smaller. Preferably, the amount of polyalkylene glycol contained in the moisturizing agent (a) is adjusted to 0.1 to 3 mass % relative to the whole cosmetic.

14 Claims, No Drawings

(56) References Cited

OTHER PUBLICATIONS

EP 12866345.7 International Search Report dated Aug. 21, 2015, 9 pages—English.
Topically applicable preparation basd on emulsion, useful for the treatment of the skin, compreises ipids, self-emulsifying emulsifier, skin moisturizing agent and/or polyols, by Heplner, Knopke, Luttig, Nielsen, Schutz, filed Apr. 2, 2009, http://www.google.sk/patets/DE102007045185A1?cl=en&hl-ja, dated Nov. 17, 2015, IFI Claims Patent Service, 9 pages—English.
EP 12 866 345.7, Office Action dated Jun. 23, 2016, 7 pages—English.

* cited by examiner

LIQUID COSMETIC

CROSS REFERENCE TO RELATED APPLICATIONS

This application claims priority to International Ser. No. PCT/JP2012/081889 filed Dec. 10, 2012, the entire contents of which are incorporated herein fully by reference, which in turn claims priority to JP Ser. No. JP 2012-006911 filed Jan. 17, 2012.

FIGURE SELECTED FOR PUBLICATION

No Figures

BACKGROUND OF THE INVENTION

Technical Field

The present invention relates to a liquid cosmetic having a high moisturizing effect as well as an excellent feeling in use. Further, the present invention relates to a liquid cosmetic that can exhibit a smooth and fresh feeling without stickiness despite formulation of a large amount of a moisturizing agent.

Background Art

For low viscous liquid cosmetics such as skin lotions, fresh and refreshing feelings are essential when they are applied to the skin.

For example, Patent Document 1 discloses that stickiness and frictional sensation caused by a salicylic acid derivative applied as a skin-whitening component in the formulation were suppressed by a microemulsion with a small amount of an oil component formulated thereinto. However, the amount of the moisturizing agent formulated in the cosmetic disclosed in Patent Document 1 is at most around 10% by mass and if the amount of the moisturizing agent is increased to the level higher than that in order to enhance the moisturizing effect, stickiness due to such amount of the moisturizing agent could not be sufficiently alleviated and richness was insufficient in some cases.

On the other hand, Patent Document 2 discloses that a sheet-like cosmetic impregnated with a cosmetic containing a tea extract and/or caffeine and sodium polyacrylate is not irritant to the skin, is excellent in skin astringent feeling and moist feeling, and has an excellent improving effect on skin sagging. Specifically, Patent Document 2 teaches that the skin irritation subject to the conventional active components such as caffeine, having a skin astringent effect, may be alleviated by sodium polyacrylate. However, the impacts on stickiness and the like due to moisturizing agents have not been investigated at all.

PRIOR ART

Patent Document

Patent Document 1: Japanese Patent Laid-Open No. 2009-242326
Patent Document 2: Japanese Patent Laid-Open No. 2011-32193

ASPECTS AND SUMMARY OF THE INVENTION

Technical Problem

Accordingly, an object of the present invention is to provide a liquid cosmetic without stickiness even when a large amount of a moisturizing agent such as polyalkylene glycol is formulated, and with richness and a fresh feeling in use.

Solution to Problem

As a result of intensive studies to solve the problem described above, the present inventors have found that further addition of polyacrylic acid to a microemulsion containing a large amount (more than 10% by mass) of a moisturizing agent not only can suppress the stickiness due to the moisturizing agent, but also can impart richness, and completed the present invention thereby.

Specifically, the present invention provides a liquid cosmetic containing: (a) a moisturizing agent 10 to 40% by mass, (b) an oil component 0.01 to 3% by mass, (c) a hydrophilic surfactant 0.01 to 5% by mass, and (d) polyacrylic acid 0.001 to 0.3% by mass or a metal salt thereof, and wherein an average emulsified particle size is 500 nm or smaller.

Advantageous Effects of Invention

The liquid cosmetic of the present invention, even containing a large amount of a moisturizing agent, suppresses the stickiness and frictional sensation due to the agent and also imparts richness and a fresh feeling, and an excellent feeling in use.

DESCRIPTION OF EXAMPLES

A moisturizing agent (component (a)) of the liquid cosmetic of the present invention may be a moisturizing agent commonly used in cosmetics, but is not particularly limited. Examples of the moisturizing agent include: saccharides or polyols such as sucrose, sorbitol, glycerin, 1,3-butylene glycol, propylene glycol, and dipropylene glycol; polyether compounds obtained by addition-polymerizing 2 to 100 mole of propylene oxide and 50 mole or less of ethylene oxide to a polyhydric alcohol core having three or more hydroxyl groups in the molecule; ethyl gluceth-10; chondroitin sulfate; hyaluronic acid; mucoitin sulfuric acid; caronic acid; atelocollagen, cholesteryl-12-hydroxystearate; bile acid monosalt; dl-pyrrolidone carboxylic acid monosalt; short-chain soluble collagen; *Rosa roxburghii* extract; *Achillea millefolium* extract; glycols such as propylene glycol, dipropylene glycol, 1,3-butylene glycol, 1,4-butylene glycol, diethylene glycol, triethylene glycol, and polyethylene glycols having a molecular weight higher than these; glycerin; diglycerin; and polyglycerins having a molecular weight higher than these; sugar alcohols such as sorbitol, mannitol, maltitol, xylitol, and erythritol; sugars such as fructose, glucose, galactose, maltose, lactose, and trehalose; and polypropyleneglycol-polyethylene glycol copolymers and dimethyl ethers thereof.

The amount of a moisturizing agent formulated in the liquid cosmetic of the present invention is from 10 to 40% by mass and preferably from 15 to 40% by mass. A higher amount of the moisturizing agent than in normal use will provide a cosmetic particularly having an excellent moisturizing effect.

Further, if a moisturizing agent formulated in a liquid cosmetic of the present invention contains polyalkylene glycol, the formulation amount thereof is preferably from 0.1 to 3% by mass of the total amount of the cosmetic. When the formulation amount of polyalkylene glycol exceeds 3% by mass, stickiness may rather be caused.

An oil component (component (b)) used in the liquid cosmetic of the present invention is preferably a liquid oil component, but is not particularly limited. Examples of the oil component include: natural oils and fats such as camellia oil, macadamia nut oil, olive oil, castor oil, safflower oil, soybean oil, tea seed oil, cacao butter, coconut oil, hydrogenated coconut oil, palm oil, Japan wax, hydrogenated castor oil, beeswax, candelilla wax, carnauba wax, lanolin, liquid lanolin, jojoba wax, hard lanolin, polyoxylethylene lanolin alcohol ether, and polyoxyethylene cholesterol ether; hydrocarbon oils and fats such as liquid paraffin, ozokerite, squalene, parffin, ceresin, petrolatum, and microcrystalline waxes; synthetic oil components such as isopropyl myristate, octyldodecyl myristate, isopropyl palmitate, cholesteryl 12-hydroxystearate, ethylene glycol di-2-ethylhexanoate, dipentaerythritol fatty acid esters, pentaerythritol tetra-2-ethylhexanoate, glycerin tri-2-ethylhexanoate, trimethylol propane triisostearate, cetyl-2-ethylhexanoate, castor oil fatty acid methyl esters and triethylhexanoin; linear polysiloxanes such as dimethylpolysiloxane, methylphenylpolysiloxane, and methylhydrogenpolysiloxane; cyclic polysiloxanes such as decamethylpolysiloxane, dodecamethylpolysiloxane, and tetramethyltetrahydrogenpolysiloxane; and silicones such as silicone resins and silicone rubbers which may form a three-dimensional network. Of these, one or two or more oil components selected from hydrocarbon oils, polar oils, silicone oils, and higher fatty acids having 12 to 22 carbon atoms are preferred, and particularly triethylhexanoin is further preferred.

The formulation amount of the oil component in the cosmetic according to the present invention is 0.01 to 3% by mass, preferably 0.05 to 2% by mass, and further preferably 0.1 to 1% by mass. When the formulation amount is less than 0.01% by mass, the improving effect on feeling in use, such as frictional sensation and stickiness, is insufficient and when the formulation amount exceeds 3% by mass, the stability of the microemulsion may decrease in some cases.

Examples of the hydrophilic surfactant (component (c)) formulated in the cosmetic of the present invention include: but are not particularly limited to; polyoxyethylene (hereinbelow, POE) sorbitan fatty acid esters such as POE sorbitan monooleate, POE sorbitan monostearate, and POE sorbitan trioleate; POE sorbit fatty acid esters such as POE sorbit monooleate, POE sorbit pentaoleate, and POE sorbit monostearate; POE glycerin fatty acid esters such as POE glycerin monostearate, POE glycerin monoisostearate, and POE glycerin isostearate; POE fatty acid esters such as POE monooleate, POE distearate, and POE dioleate; POE alkyl ethers such as POE oleyl ether, POE stearyl ether, POE behenyl ether, POE2-octyldodecyl ether, POE2-hexyldecyl ether, POE2-heptylundecyl ether, POE2-decyltetradecyl ether, POE2-decylpentadecyl ether, and POE cholestanol ether; POE alkylphenyl ethers such as POE nonylphenyl ether; POE-POP block copolymers; POE-POP alkyl ethers such as POE-POP cetyl ether, POE-POP2-decyltetradecyl ether, and POE-POP hydrogenated lanolin; POE castor oil or hydrogenated castor oil derivatives such as POE castor oil; POE beeswax-lanolin derivatives such as POE sorbit beeswax; POE phytosterol ether; and POE polyether-modified silicone surfactants. Of these, hydrophilic nonionic surfactants selected from polyoxyalkylene-added alkyl ethers, polyoxyalkylene-added alkyl esters, polyoxyalkylene-added sorbitan, polyoxyalkylene-added hydrogenated castor oil, polyoxyalkylene-added phytosterol, or hydrophilic anionic surfactants, having an HLB of 13 or higher, selected from N-acyl glutamate and acylalkyl taurate are preferred. Particularly, POE-hydrogenated castor oil and POE phytosterol ether are preferred.

The amount of the hydrophilic surfactant formulated in the cosmetic of the present invention is generally 0.01 to 5% by mass, preferably 0.05 to 3% by mass, and further preferably 0.1 to 1% by mass. When the formulation amount is less than 0.01% by mass, the emulsion stability may decrease, and when the formulation amount exceeds 5% by mass, the usability may decrease because of increased stickiness or the like.

The liquid cosmetic of the present invention further contains polyacrylic acid or a metal salt thereof (component (d)) as an essential component.

The polyacrylic acid used in the present invention may be selected from thickeners conventionally used in cosmetics or the like, but is not particularly limited and commercially available products may also be used.

In the present invention, examples of the metal salt of polyacrylic acid include salts of alkali metals such as sodium and potassium.

The number average molecule weight of the polyacrylic acid is normally from 10,000 to 250,000, preferably 10,000 to 100,000, and further preferably from 10,000 to about 50,000, but is not particularly limited.

The amount of polyacrylic acid formulated in the liquid cosmetic of the present invention is 0.001 to 0.3% by mass, preferably 0.002 to 0.2% by mass, and further preferably 0.003 to 0.1% by mass. When the formulation amount is less than 0.001% by mass, the suppressing effect on stickiness is insufficient, and when the formulation amount exceeds 0.3% by mass, good spreadability and a fresh feeling specific to liquid cosmetics may be lost because of increased viscosity in some cases.

A lipophilic surfactant (component (e)) having an HLB of 7 or smaller is preferably further formulated in the liquid cosmetic of the present invention. Examples of the lipophilic surfactant having an HLB of 7 or smaller formulated in the cosmetic of the present invention include, but are not particularly limited to, polyglyceryl-2 diisostearate, polyoxyethylene fatty acid glyceryl, polyoxyethylene-methylpolysiloxane copolymer, fatty acid sorbitan, fatty acid polyoxyethylene sorbitan, polyoxyethylene alkyl ether, polyglycol fatty acid ester, alkaloyl diethanolamide, and fatty acid isopropanolamide, and polyglyceryl-2 diisostearate is particularly preferred.

The formulation amount of the lipophilic surfactant in the liquid cosmetic of the present invention is preferably 0.01 to 5% by mass and further preferably 0.1 to 3% by mass. When the formulation amount is less than 0.01% by mass, the formulation effects (on such as increase of emulsion stability) cannot be obtained, and when the formulation amount exceeds 5% by mass, usability may decrease because of stickiness or the like in some cases.

In the liquid cosmetic of the present invention, it is preferred that formulated oily, aqueous, and amphipathic components form a system (a microemulsion in a narrow sense) in which thermodynamically stable, and swollen large micelles are dispersing in a transparent or translucent single liquid phase. However, the microemulsion of the present invention includes microemulsions in a broad sense, in which a thermodynamically unstable dispersed system and a transparent or translucent dispersed system that is stable over time are included.

The microemulsion constituting the cosmetic of the present invention has an average emulsified particle size from 10 to 500 nm and a viscosity of 2000 mPa·s (at 30° C.) or less, particularly preferably 300 mPa·s or less.

The liquid cosmetic of the present invention can be produced by, for example, a first step of mixing the components (b) and (c) (and optionally further (e)), and heating the mixture to 70° C. to prepare a single phase microemulsion composition, and subsequently a second step of diluting the composition in a phase containing water (containing the components (a) and (d)).

Other additives may be formulated in the liquid cosmetic of the present invention as needed, and types and formulation amounts are appropriately selected to the extent in that the effects of the present invention are not impaired. Examples of the other additives include perfumes, pigments, buffers, salts, skin-whitening agents, preservatives, antioxidant perfume, coloring agents and other powders, medicaments, thickeners, ultraviolet absorbents, and activation aids.

The liquid cosmetic of the present invention is preferably provided as a transparent and/or translucent skin lotion, an essence (beauty liquid) and the like. By adopting such a constitution, an excellent feeling in use is achieved while an excellent moisturizing effect is exploited.

EXAMPLES

Hereinbelow, the invention is described in further detail referring to specific examples, but these are not intended to limit the technical scope of the present invention in any aspect. It should be noted that the formulation amounts in Examples, Comparative Examples, and Formulation Examples below are all expressed in % by mass.

Liquid cosmetics having the composition shown in Tables 1 to 3 were prepared.

Then, an actual use test on these liquid cosmetics was carried out by 20 expert panelists. Test items include non-stickiness, non-frictional sensation, richness, and freshness. Each expert panelist evaluated and scored each item based on the evaluation score criteria below. Depending on the total evaluation score, the cosmetics were ranked into four grades. The result of ranking is also shown in Tables 1 to 3.

Evaluation score criteria (non-stickiness, non-frictional sensation, richness, and freshness):
  5: Excellent
  4: Good
  3: Fair
  2: Poor
  1: Very poor
Evaluation Grades:
  A: Total score of 80 or more
  B: Total score of 60 or more and less than 80
  C: Total score of 40 or more and less than 60
  D: Total score of less than 40

TABLE 1

|  | Example 1 | Example 2 | Example 3 | Comparative Example 1 | Comparative Example 2 | Comparative Example 3 |
| --- | --- | --- | --- | --- | --- | --- |
| Triethylhexanoin | 0.01 | 0.01 | 0.01 | — | 0.01 | 0.01 |
| POE hydrogenated castor oil (60) | 0.2 | 0.2 | 0.2 | 0.2 | 0.2 | 0.2 |
| Polyglyceryl-2 diisostearate | 0.2 | 0.2 | 0.2 | 0.2 | 0.2 | 0:2 |
| Methyl gluceth-10 | 0.5 | 0.5 | 0.5 | 0.5 | 0.5 | 0.5 |
| Polyethylene glycol 20000 | 1 | 1 | 1 | 1 | 1 | 1 |
| Na polyacrylate | 0.001 | 0.01 | 0.3 | — | — | 0.4 |
| Glycerin | 10 | 10 | 10 | 10 | 10 | 10 |
| Butylene glycol | 6 | 6 | 6 | 6 | 6 | 6 |
| Phenoxyethanol | 0.3 | 0.3 | 0.3 | 0.3 | 0.3 | 0.3 |
| Ethanol | 5 | 5 | 5 | 5 | 5 | 5 |
| Citric acid | Appropriate amount | Appropriate amount | Appropriate amount | Appropriate amount | Appropriate amount | Appropriate amount |
| Sodium citrate | Appropriate amount | Appropriate amount | Appropriate amount | Appropriate amount | Appropriate amount | Appropriate amount |
| Edetate | Appropriate amount | Appropriate amount | Appropriate amount | Appropriate amount | Appropriate amount | Appropriate amount |
| Perfume | Appropriate amount | Appropriate amount | Appropriate amount | Appropriate amount | Appropriate amount | Appropriate amount |
| Water | Balance | Balance | Balance | Balance | Balance | Balance |
| Average emulsified particle size (nm) | 150 | 150 | 150 | — | 150 | 150 |
| Non-Stickiness | B | A | B | C | D | C |
| Richness | B | A | A | C | C | A |
| Freshness | B | B | B | B | B | C |

TABLE 2

|  | Example 4 | Example 5 | Comparative Example 4 | Comparative Example 5 |
| --- | --- | --- | --- | --- |
| Triethyl-hexanoin | 0.01 | 1 | — | 5 |
| POE hydrogenated castor oil (60) | 0.2 | 0.2 | 0.2 | 10 |
| Polyglyceryl-2 diisostearate | 0.2 | 0.2 | 0.2 | 10 |

TABLE 2-continued

|  | Example 4 | Example 5 | Comparative Example 4 | Comparative Example 5 |
|---|---|---|---|---|
| Na polyacrylate | 0.005 | 0.005 | 0.005 | 0.005 |
| Polyethylene glycol 20000 | 1 | 1 | 1 | 1 |
| Methyl gluceth-10 | 0.5 | 0.5 | 0.5 | 0.5 |
| Butylene glycol | 6 | 6 | 6 | 6 |
| Glycerin | 10 | 10 | 10 | 10 |
| Phenoxyethanol | 0.3 | 0.3 | 0.3 | 0.3 |
| Ethanol | 5 | 5 | 5 | 5 |
| Perfume | Appropriate amount | Appropriate amount | Appropriate amount | Appropriate amount |
| Citric acid | Appropriate amount | Appropriate amount | Appropriate amount | Appropriate amount |
| Sodium citrate | Appropriate amount | Appropriate amount | Appropriate amount | Appropriate amount |
| Edetate | Appropriate amount | Appropriate amount | Appropriate amount | Appropriate amount |
| Water | Balance | Balance | Balance | Balance |
| Average emulsified particle size (nm) | 150 | 200 | — | 300 |
| Non-Stickiness | B | B | C | D |
| Non-Frictional sensation | B | B | C | C |
| Freshness | B | B | B | C |
| Richness | B | B | B | B |

According to the results shown in Table 1, when polyacrylic acid 0.001 to 0.3% by mass is formulated, stickiness was suppressed and richness and a fresh feeling were obtained even with the cosmetics containing 17.5% by mass of total moisturizing agents (Examples 1 to 3.) In contrast, in Comparative Example 1 without oil component and Comparative Example 2 with oil and no polyacrylic acid, stickiness was felt and richness was poor. Further, Comparative Example 3 containing more than 0.3% by mass of polyacrylic acid had an excellent richness, but had stickiness and lacked freshness.

According to the results in Table 2, polyacrylic acid 0.005% by mass suppressed stickiness and frictional sensation, even though the amount of the oil component varied between 0.01 and 1% by mass (Examples 4 and 5), but no effect was achieved without oil (Comparative Example 4), and conversely, when the amount of the oil component was 5% by mass, stickiness emerged and freshness was lost because the surfactant necessary to emulsify the component increased (Comparative Example 5.)

The results in Table 3 show that addition of polyacrylic acid reduced stickiness and frictional sensation due to the cosmetics containing 15.5% by mass of total moisturizing agents (Examples 6 and 7, and Comparative Example 6.) Additionally, it was shown that when the amount of polyalkylene glycol contained in the moisturizing agent exceeded 3% by mass, excellent richness was obtained but stickiness (nevertheless problematic in actual use) could

TABLE 3

|  | Example 6 | Example 7 | Comparative Example 6 | Example 8 | Example 9 |
|---|---|---|---|---|---|
| Triethylhexanoin | 0.01 | 0.01 | 0.01 | 0.01 | 0.01 |
| POE hydrogenated castor oil (60) | 0.2 | 0.2 | 0.2 | 0.2 | 0.2 |
| Polyglyceryl-2 diisostearate | 0.2 | 0.2 | 0.2 | 0.2 | 0.2 |
| Methyl gluceth-10 | 0.5 | 0.5 | 0.5 | 0.5 | 0.5 |
| Polyethylene glycol 20000 | 1 | 1 | 1 | 3 | 5 |
| Na polyacrylate | 0.003 | 0.01 | — | 0.3 | 0.3 |
| Glycerin | 8 | 8 | 8 | 8 | 8 |
| Carboxyvinyl polymer | — | — | 0.2 | — | — |
| Butylene glycol | 6 | 6 | 6 | 6 | 6 |
| Phenoxyethanol | 0.3 | 0.3 | 0.3 | 0.3 | 0.3 |
| Ethanol | 5 | 5 | 5 | 5 | 5 |
| Citric acid | Appropriate amount | Appropriate amount | Appropriate amount | Appropriate amount | Appropriate amount |
| Sodium citrate | Appropriate amount | Appropriate amount | Appropriate amount | Appropriate amount | Appropriate amount |
| Edetate | Appropriate amount | Appropriate amount | Appropriate amount | Appropriate amount | Appropriate amount |
| Perfume | Appropriate amount | Appropriate amount | Appropriate amount | Appropriate amount | Appropriate amount |
| Caustic potash | — | — | Appropriate amount | — | — |
| Water | Balance | Balance | Balance | Balance | Balance |
| Average emulsified particle size (nm) | 150 | 150 | 150 | 150 | 150 |
| Non-Stickiness | B | A | D | B | C |
| Non-Frictional sensation | B | B | C | B | B |
| Richness | B | A | B | A | A |
| Freshness | B | B | C | B | B | occur more or less as compared with the cases where the amount of polyalkylene glycol was 3% by mass or less (Examples 8 and 9.)

Formulation Example 1

Skin Lotion:

| Formulation Components | Formulation amount (% by mass) |
|---|---|
| (A) | |
| POE hydrogenated castor oil (60) | 0.2 |
| Polyglyceryl-2 diisostearate | 0.2 |
| Triethylhexanoin | 0.1 |
| Methyl gluceth-10 | 0.5 |
| Perfume | Appropriate amount |
| Butylene glycol | 6.0 |
| (B) | |
| Glycerin | 8.0 |
| Na polyacrylate | 5 |
| Phenoxyethanol | 0.3 |
| Water | Balance |
| Alkoxy salicylate | 1.0 |
| Polyethylene glycol 20000 | 1.0 |
| Ethanol | 5.0 |

Production Method:

Components of A were mixed and dissolved at 70° C. This was added to the mixed solution of B under stirring and emulsified to obtain a skin lotion. Average particle size: 200 nm.

Formulation Example 2

Skin-Whitening Milky Beauty Liquid:

| Formulation Components | Formulation amount (% by mass) |
|---|---|
| (A) | |
| Polyoxyethylene methylglucoside | 1.0 |
| Isostearic acid | 0.2 |
| Glyceryl tri(2-ethylhexanoate) | 0.3 |
| Polyoxyethylene (30) phytosterol | 0.09 |
| Sorbitan sesquiisostearate | 0.03 |
| (B) | |
| Glycerin | 8.0 |
| Citric acid | Appropriate amount |
| Sodium citrate | Appropriate amount |
| Potassium hydroxide | Appropriate amount |
| Dipotassium glycyrrhizate | 0.1 |
| Arginine hydrochloride | 0.1 |
| Ethanol | 1.0 |
| Dipropylene glycol | 10.0 |
| Polyethylene glycol 1000 alkoxy salicylate | 0.6 |
| *Scutellaria baicalensis* extract | 1.0 |
| *Saxifrage sarmentosa* extract | 0.1 |
| Dead nettle extract | 0.1 |
| Tranexamic acid | 0.1 |
| Trisodium edetate | 1.0 |
| 2-Ethylhexyl para-methoxycinnamate | 0.05 |
| Dibutylhydroxytoluene | 0.01 |
| Na polyacrylate | 0.008 |
| Polyethylene glycol 6000 | 1.0 |
| Paraben | Appropriate amount |
| Deep ocean water | Appropriate amount |
| Purified water | Balance |
| Perfume | Appropriate amount |

Production Method:
Production Method:

A layered heat-dissolved surfactants/oil component (A) was added under stirring to a stir-dissolved water phase (B) to obtain a milky beauty liquid. Average particle size: 200 nm.

Having described at least one of the preferred embodiments of the present invention, it will be apparent to those skills that the invention is not limited to those precise embodiments, and that various modifications and variations can be made in the presently disclosed cosmetic and method without departing from the scope or spirit of the invention. Thus, it is intended that the present disclosure cover modifications and variations of this disclosure provided they come within the scope of the appended claims and their equivalents.

What is claimed is:

1. A liquid cosmetic comprising:
   (a) a moisturizing agent in a concentration of 15 to 40% by mass,
   (b) an oil component in a concentration of 0.01 to 3% by mass,
   (c) a hydrophilic surfactant which is a polyoxyethylene (POE)-hydrogenated castor oil having a HLB of 13 or higher in a concentration of 0.01 to 5% by mass
   (d) polyacrylic acid and/or a metal salt thereof in a concentration of 0.001 to 0.3% by mass, wherein the liquid cosmetic exhibits reduced stickiness relative to the same composition not containing 0.001 to 0.3% by mass polyacrylic acid and/or a metal salt thereof; and
   (e) water
   wherein the composition is an oil-in-water emulsion having an average emulsified particle size of 500 nm or smaller.

2. A liquid cosmetic according to claim 1, further comprising (f) a lipophilic surfactant having an HLB of 7 or smaller.

3. The liquid cosmetic according to claim 1, wherein:
   the hydrophilic surfactant (c) is POE hydrogenated caster oil (60).

4. The liquid cosmetic according to claim 1, wherein:
   the moisturizing agent (a) is selected from the group consisting of: sucrose, fructose, glucose, galactose, maltose, lactose, trehalose, sorbitol, mannitol, xylitol, erythritol, glycerin, 1,3-butylene glycol, propylene glycol, dipropylene glycol, chondroitin sulfate, hyaluronic acid, and atelocollagen.

5. The liquid cosmetic according to claim 1, wherein:
   the oil component (b) is selected from the group consisting of camellia oil, macadamia nut oil, olive oil, castor oil, safflower oil, soybean oil, tea seed oil, cacao butter, coconut oil, hydrogenated coconut oil, palm oil, beeswax, candelilla wax, carnauba wax, lanolin, jojoba wax, liquid paraffin, ozokerite, aqualene, paraffin, ceresin, petrolatum, isopropyl myristate, octyldodecyl myristate, isopropyl palmitate, cholesteryl 12-hydroxystearate, dimethylpolysiloxane, methylphenylpolysiloxane, methylhydrogenpolysiloxane, decamethylpolysiloxane, dodecametlaylpolysiloxane, tetramethyltetrahydrogenpolysiloxane, and triethylhexanoin.

6. The liquid cosmetic according to claim 1, wherein:
   the moisturizing agent (a) is glycerin, the oil phase (b) is triethylhexanoin, and the hydrophilic surthetant (c) is POE hydrogenated castor oil (60).

7. The liquid cosmetic according to claim 6, further comprising:
   polyethylene glycol 20000 in a concentration of 1% by mass.

8. The liquid cosmetic according to claim 6, further comprising:
   butylene glycol in a concentration of 6% by mass.

9. The liquid cosmetic according to claim 6, further comprising:
   phenoxyethanol in a concentration of 0.3% by mass.

10. The liquid cosmetic according to claim 6, further comprising:
    ethanol in a concentration of 5% by mass.

11. The liquid cosmetic according to claim 6, further comprising:
    citric acid and sodium citrate.

12. The liquid cosmetic according to claim 6, further comprising:
    perfume.

13. The liquid cosmetic according to claim 6, further comprising:
    edetate.

14. The liquid cosmetic according to claim 1, wherein:
    the average emulsified particle size is 150 nm.

* * * * *